US009796785B2

(12) United States Patent  
Okuda

(10) Patent No.: US 9,796,785 B2  
(45) Date of Patent: Oct. 24, 2017

(54) MONOCLONAL ANTIBODY RECOGNIZING SIALYLATED SUGAR CHAINS

(71) Applicant: NATIONAL INSTITUTE OF ADVANCED INDUSTRIAL SCIENCE AND TECHNOLOGY, Tokyo (JP)

(72) Inventor: Tetsuya Okuda, Sapporo (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 0 days.

(21) Appl. No.: 14/888,147

(22) PCT Filed: May 2, 2014

(86) PCT No.: PCT/JP2014/002402  
§ 371 (c)(1),  
(2) Date: Oct. 30, 2015

(87) PCT Pub. No.: WO2014/178196  
PCT Pub. Date: Nov. 6, 2014

(65) Prior Publication Data  
US 2016/0068611 A1  Mar. 10, 2016

(30) Foreign Application Priority Data  
May 2, 2013 (JP) ................. 2013-096866

(51) Int. Cl.  
*C12N 5/12* (2006.01)  
*C07K 16/40* (2006.01)  
*G01N 33/574* (2006.01)  
*C12N 9/10* (2006.01)  
*C07K 16/28* (2006.01)

(52) U.S. Cl.  
CPC .......... *C07K 16/40* (2013.01); *C07K 16/2896* (2013.01); *C12N 9/1081* (2013.01); *G01N 33/57419* (2013.01); *G01N 33/57446* (2013.01); *G01N 33/57492* (2013.01); *C07K 2317/14* (2013.01); *C07K 2317/30* (2013.01); *C07K 2317/92* (2013.01); *C12Y 204/99001* (2013.01); *G01N 2333/91148* (2013.01); *G01N 2440/38* (2013.01)

(58) Field of Classification Search  
CPC ... C07K 16/28; C07K 16/2896; G01N 33/574  
USPC ...... 530/387.5; 424/137.1; 435/325, 329, 7.4  
See application file for complete search history.

(56) References Cited

FOREIGN PATENT DOCUMENTS

JP  2002-528037 A  8/2002

OTHER PUBLICATIONS

Gramatzki et al. (Ann Hematol, 1991, 63: 20-26).*  
Stratagene Catalog 1988, p. 39.*  
International Search Report dated Jul. 22, 2014, issued in counterpart International Application No. PCT/JP2014/002402 (2 pages).  
Suzuki, "Sialobiology of Influenza Molecular Mechanism of Host Range Variation of Influenza Viruses", Biol. Pharm. Bull., Mar. 2005, pp. 399-408, vol. 28, No. 3.  
Guy et al., "Expression of the CDw75 (beta-galactoside alpha 2,6-sialyltransferase) antigen on normal blood cells and in B-cell chronic lymphocytic leukaemia", Immunology, Jun. 20, 1991, pp. 206-214, vol. 74.  
Costa-Nogueira et al., "Synthesis and expression of CDw75 antigen in human colorectal cancer", BMC Cancer, Dec. 10, 2009, vol. 9, Article: 431, (10 pages).  
Bast et al., "The HB-6, CDw75, and CD76 Differentiation Antigens are Unique Cell-Surface Carbohydrate Determinants Generated by the beta-Galactoside alpha2,6-Sialyltransferase", The Journal of Cell Biology, Jan. 1992, pp. 423-435, vol. 116, No. 2.  
Ozawa et al., "Generation and Characterization of Mouse Monoclonal Antibodies Specific for N-Linked Neutral Oligosaccharides of Glycoproteins", Archives of Biochemistry and Biophysics, Jun. 1, 1997, pp. 48-57, vol. 342, No. 1.  
Murakami et al., "Convenient preparation and characterization of a monoclonal antibody for the N-linked sugar chain of a glycoprotein using a microbial endoglycosidase", Archives of Biochemistry and Biophysics, 2008, pp. 299-304, vol. 477.  
Notification of Transmittal of Translation of the International Preliminary Report on Patentability (Forms PCT/IB/326) issued in counterpart International Application No. PCT/JP2014/002402 dated Nov. 12, 2015, with Forms PCT/IB/373, PCT/IB/338 and PCT/ISA/237. (10 pages).  
Extended (supplementary) European Search Report dated Jan. 24, 2017, issued in counterpart European Patent Application No. 14792262.9. (8 pages).  
M. Liedtke, et al. "Phase I trial of a novel human monoclonal antibody mAb216 in patients with relapsed or refractory B-cell acute lymphoblastic leukemia", Haematologica, 2012, vol. 97, No. 1, pp. 30-37. Cited in extended (supplementary) European Search Report dated Jan. 24, 2017.

(Continued)

*Primary Examiner* — Yan Xiao  
(74) *Attorney, Agent, or Firm* — Westerman, Hattori, Daniels & Adrian, LLP

(57) ABSTRACT

The purpose of the present invention is to provide a novel monoclonal antibody having high affinity and that strictly recognizes, as a sugar chain epitope, only a "Siaα2,6Galβ1,4GlcNAc (6'-Sialyl-LacNAc): CDw75" sugar chain structure, being a molecular target for diagnosis of the malignancy of tumors. An anti-CDw75 monoclonal antibody is provided that recognizes "CDw75" sugar chain structures but does not recognize similar sugar chain structures indicated by "Galβ1,4GlcNAc", "Siaα2,3Galβ1,4GlcNAc", or "Siaα2,6Galβ1,4Glc", by using a glycolipid antigen bonding a carrier lipid compound "HOCH$_2$CH(NH—CO—(CH$_2$)$_{22}$—CH$_3$)—(CH$_2$)$_9$—CH$_3$ (C12L)" developed by the inventors to a "CDw75" sugar chain. The obtained anti-CDw75 monoclonal antibody is an excellent detection drug for B-cell lymphoma, gastric cancer, or colorectal cancer, an excellent diagnostic agent for tumor malignancy, etc., an excellent treatment agent for B-cell lymphoma, gastric cancer, or colorectal cancer, and an excellent prevention/treatment drug for influenza.

4 Claims, 3 Drawing Sheets

(56) References Cited

OTHER PUBLICATIONS

L. David, et al. "CDw75 Antigen Expression in Human Gastric Carcinoma and Adjacent Mucosa", Cancer, 1993, vol. 72, No. 5, pp. 1522-1527. Cited in extended (supplementary) European Search Report dated Jan. 24, 2017.

G. Elpek, et al. "Clinicopathologic Evaluation of CDw75 Antigen Expression in Colorectal Adenocarcinomas", Pathology Oncology Research: 2002, vol. 8, No. 3, pp. 175-182. Cited in extended (supplementary) European Search Report dated Jan. 24, 2017.

* cited by examiner

MONOCLONAL ANTIBODY RECOGNIZING SIALYLATED SUGAR CHAINS

TECHNICAL FIELD

The present invention relates to a monoclonal antibody having high affinity which specifically recognizes "6'-Sialyl-LacNAc (Siaα2,6Galβ1,4GlcNAc): CDw75" of a sialylated sugar chain, a composition for detection, diagnosis, and treatment of gastric cancer or colorectal cancer or a composition for prevention and treatment of influenza using the monoclonal antibody. The present invention also relates to a kit for analyzing a sugar chain based on ELISA or Western blot using the monoclonal antibody.

BACKGROUND ART

In mammalian cells, sugar chains having a special structure reflecting each cell type, stage of development and differentiation, disease conditions, or the like are expressed. In the form of a glycoprotein or glycolipid, the sugar chains are present on a surface layer of a cell or in blood serum. Based on their properties, determination is made on their effective use as a biomarker like proteins and nucleic acids. In recent years, it is also found that the sugar chains play an important role in vivo, and thus studies on their function are also carried out. For example, "Siaα2,6Gal" or "Siaα2,3Gal" of a sialylated sugar chain is a sugar chain which is broadly present on a surface of lymphocyte involved with immunological response, and thus a pharmaceutical agent for detecting those sialylated sugar chains is employed as an indicator of immunodeficiency (Patent Literature 1).

However, compared to proteins and nucleic acids, the technique relating to structure identification or detection of sugar chains is not sufficiently established. Once an antibody capable of identifying and detecting a partial structure of the sugar chain, which specifies the structure of the sugar chain, is developed, it can be not only a huge advantage for fast and accurate diagnosis and development of a therapeutic agent for various malignant tumors and various symptoms, but also a simple sugar chain analysis based on ELISA or Western blot, both widely employed for protein analysis, can be achieved, and thus it is believed that further research and development regarding sugar chain function and industrial application can be promoted.

Among the oligosaccharide chains of an N-linked glycoprotein, the sugar chain structure represented by "6'-Sialyl-LacNAc (Siaα2,6Galβ1,4GlcNAc)" is also referred to as "CDw75", and it is a structure shown in a glycoprotein or a glycolipid that is expressed in mammalian cells. This sugar chain structure is known to be an infection receptor of human influenza virus (Non Patent Literature 1), and it has also been identified as a cell surface layer marker of B-cell lymphoma (Non Patent Literature 2) or an epitope of a novel tumor marker (CDw75) having a relationship with the malignancy of gastric cancer or colorectal cancer (Non Patent Literature 3). Based on the relationship with those serious diseases, determination has been made on the effective use as a diagnosis indicator. In particular, it is highly expected to be used as a molecular target for determination and diagnosis of malignancy of gastric cancer or colorectal cancer, or treatment of malignant tumors such as B-cell lymphoma.

CDw75 is an antigen defined as a cell surface layer antigen that is commonly recognized by four kinds of a monoclonal antibody obtained by immunization of lymphocytes (Non Patent Literature 4), and it is expressed in mature B cells or in part of T cells in peripheral blood. As a partial epitope that is commonly recognized by those four kinds of the antibody, a sugar chain antigen represented by Siaα2,6Galβ1,4GlcNAc has been originally identified and found to be an essence of CDw75 (Non Patent Literature 3). However, it was also known that the antibody specificity is different among those four kinds of the antibody. It is believed that each antibody recognizes a different biomolecule with CDw75, including CDw75 and neighboring regions as an epitope. Among those four kinds of the antibody, most widely used antibody is LN-1 monoclonal antibody, which is also commercially available (Santacruz Biotechnology). However, due to insufficient affinity and specificity for CDw75, its use is limited to an immunohistochemical examination (Non Patent Literature 3).

When an oligosaccharide chain is used as an antigen, there is only insufficient development of an immune system which recognizes sugar chains in vivo of a mammalian. As such, it is generally difficult to produce an antibody which recognizes the oligosaccharide chain itself as an epitope. It is known that, although the sugar chains derived from microorganisms can be easily recognized, it is difficult to produce an antibody which recognizes a sugar chain antigen of a glycoprotein derived from mammalian, in particular, an oligosaccharide chain antigen included in N-linked sugar chains (Non Patent Literature 5 and Non Patent Literature 6). Even at the present moment, an effective antibody having the N-linked sugar oligosaccharide chain antigen itself of a glycoprotein as an epitope is hardly developed.

With regard to an antibody recognizing CDw75 as an epitope, there is a report of CDw75 monoclonal antibody which is obtained by a method of immune induction by using phosphatidyl ethanolamine as a carrier compound and using, as an immunogen, a compound obtained by conjugation of an oligosaccharide chain containing CDw75 in a reductive manner to the amino group of the carrier compound (Non Patent Literature 6). However, the obtained CDw75 monoclonal antibody has insufficient practical value as well as insufficient affinity and specificity.

As described above, although there is high expectancy for CDw75 sugar chain as a diagnostic agent or a molecular target for therapeutics, an antibody having practical value as well as high affinity and specificity, in which CDw75 itself is an epitope, does not exist up until now. Under the circumstances, development of an antibody with practical value enabling direct and accurate detection of CDw75 is waited for.

CITATION LIST

Patent Literature

Patent Literature 1: JP 2002-528037 W

Non Patent Literatures

Non Patent Literature 1: Suzuki Y. (2005) Biol. Pharm. Bull. 28, 399-408.
Non Patent Literature 2: Guy K. and Andrew J M. (1991) Immunology, 74, 206-214.
Non Patent Literature 3: Costa-Nogueira C., et al. (2009) BMC Cancer. 9, 431.
Non Patent Literature 4: Bast B J., et al. (1992) J. Cell Biol. 116, 423-435.
Non Patent Literature 5: Ozawa H., et al. (1997) Arch. Biochem. Biophys. 342, 48-57.
Non Patent Literature 6: Murakami D., et al. (2008) Arch. Biochem. Biophys. 477, 299-304.

SUMMARY OF INVENTION

Technical Problem

The present invention is to provide a novel monoclonal antibody having high affinity and that strictly recognizes, as a sugar chain epitope, only a "Siaα2,6Galβ1,4GlcNAc (6'-Sialyl-LacNAc): CDw75" sugar chain structure, being a molecular target for diagnosis of the malignancy of tumors, treatment of malignant tumors, or treatment of influenza or the like. The present invention is also to provide a monoclonal antibody which can be applied to Western blot as a general method for analysis of proteins.

In addition, the present invention is to provide a method for diagnosis and a kit for diagnosis of B-cell lymphoma, gastric cancer, or colorectal cancer using the monoclonal antibody of the present invention, and also a method for screening a therapeutic agent for tumors with high malignancy.

Solution to Problem

Inventors of the present invention successfully developed a carrier compound allowing enhancement of immunogenicity of a certain oligosaccharide chain. Furthermore, according to application of the technique, an immunity inducing agent consisting of a target oligosaccharide chain and a carrier compound was developed, and it was filed as a patent application on the same day.

According to the present invention, a monoclonal antibody was produced by a common method by applying the immunity-inducing method to "6'-Sialyl-LacNAc (Siaα2,6Galβ1,4GlcNAc): CDw75" as a target oligosaccharide chain.

As a result, it was possible to select a hybridoma cell which produces a monoclonal antibody with very high specificity recognizing, as an epitope, a target oligosaccharide chain (6'-Sialyl-LacNAc) but not recognizing at all LacNAc (Galβ1,4GlcNAc) as a precursor and 3'-Sialyl-LacNAc (Siaα2,3Galβ1,4GlcNAc) and 6'-Sialyllactose (Siaα2,6Galβ1,4Glc), which have a structure most similar to the target oligosaccharide chain among sugar chains present in mammalian body. Furthermore, when determined from the dissociation constant for the glycoprotein modified with CDw75 (Fetuin), it was found to have very high affinity.

That is, the present invention includes the followings:
[1] An anti-CDw75 monoclonal antibody or a fragment thereof, characterized in that which recognizes sugar chain structure CDw75 represented by Siaα2,6Galβ1,4GlcNAc but not a sugar chain structure represented by Galβ1,4GlcNAc; Siaα2,3Galβ1,4GlcNAc; or 6'-Sialyllactose (Siaα2,6Galβ1,4Glc).
[2] The anti-CDw75 monoclonal antibody or a fragment thereof according to [1], wherein glycolipid antigen CDw75-C12L represented by the following general formula (2) is used as an immunogen.

[Chemical Formula 1]

[3] The anti-CDw75 monoclonal antibody or a fragment thereof according to [1] or [2], the antibody being produced by hybridoma FR9 (deposit number: NITE BP-01516).
[4] A composition including the anti-CDw75 monoclonal antibody or a fragment thereof according to any of [1] to [3], and a pharmaceutically acceptable carrier.
[5] The pharmaceutical composition according to [4], the composition being used for inhibition and/or treatment of B-cell lymphoma, gastric cancer, or colorectal cancer.
[6] The pharmaceutical composition according to [4], the composition being used for prevention and/or treatment of influenza.
[7] The composition according to [4], the composition being used for detection and/or diagnosis of B-cell lymphoma, gastric cancer, or colorectal cancer.
[8] A method for detection and/or quantification of sugar chain antigen CDw75 by using the anti-CDw75 monoclonal antibody or a fragment thereof according to any of [1] to [3].
[9] A kit for determining morbidity and/or tumor malignancy of gastric cancer or colorectal cancer, the kit including as an effective component the anti-CDw75 monoclonal antibody or a fragment thereof according to any of [1] to [3].
[10] A method for purification of a compound having sugar chain antigen CDw75 by using the anti-CDw75 monoclonal antibody or a fragment thereof according to any of [1] to [3].
[11] A method for isolation of a cell having sugar chain antigen CDw75 by using the anti-CDw75 monoclonal antibody or a fragment thereof according to any of [1] to [3].
[12] Hybridoma FR9 which produces anti-CDw75 monoclonal antibody (deposit number: NITE BP-01516).

Advantageous Effects of Invention

The monoclonal antibody obtained from the present invention has very strict epitope recognition specificity for "CDw75" sugar chain structure and also very high affinity therefor. As such, the monoclonal antibody can be an effective tool for diagnosis of B-cell lymphoma, gastric cancer, and colorectal cancer, and it can be also effectively used for screening of a therapeutic agent for tumor with high malignancy.

Furthermore, it can be also used not only for detection at cellular or tissue level and flow cytometry or immunohistochemistry as an analytical method but also for Western blot generally used for protein analysis and analysis at molecular level of a protein.

In particular, Western blot is a simple analytical method which allows separation and detection of proteins based on molecular weight or isoelectric point, and it allows easy determination of the presence of a sugar chain epitope in a protein as a subject for analysis.

Furthermore, as the monoclonal antibody of the present invention recognizes "CDw75" sugar chain structure as an epitope, regardless of glycolipid or glycoprotein, any substance can be detected as long as it contains that oligosaccharide chain. By taking advantage of this characteristic, if it is applied, in combination with an antibody which recognizes a core protein area of a glycoprotein, to sandwich ELISA or immunochromatography as a basic technique for a diagnosing agent, detection with even higher sensitivity can be achieved.

General formula (2)

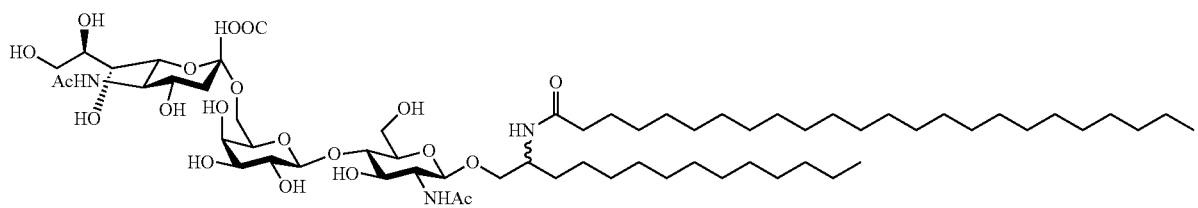

BRIEF DESCRIPTION OF DRAWINGS

FIG. 1A: With regard to the affinity of the FR9 antibody for an epitope, a dissociation constant (Kd value) having a glycoprotein which includes CDw75 sugar chain (Fetuin) as an antigen was determined based on ELISA and Scatchard plot. On the x axis, a value obtained by dissociating the amount of antigen and antibody complex (Ag-Ab) by the total amount of antibody (Abt), that is, (Ag-Ab/Abt), is plotted, and on the y axis, a value obtained by dissociating the (Ag-Ab/Abt) by the total amount of free antigen (Agf), that is, (Ag-Ab/Abt.Agf), is plotted. As the slope of the approximated curve of each plot (y=−0.11x+0.11) is −1/Kd, Kd value ($8.86 \times 10^{-7}$ M) was calculated from the slope. FIG. 1B: With regard to the affinity of the FR9 antibody for an epitope, the detection sensitivity was measured by ELISA which uses, as an antigen, a glycoprotein including CDw75 sugar chain (Fetuin: empty circle) and the immunogen (CDw75-C12L: filled circle).

DESCRIPTION OF EMBODIMENTS

Figure 1:
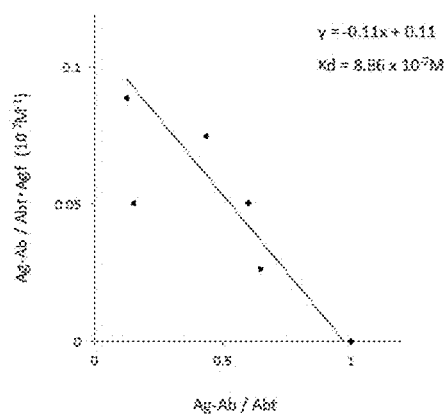
FIGS. 1A and 1B show affinity of the developed monoclonal antibody FR9 for epitope.
Figure 1:
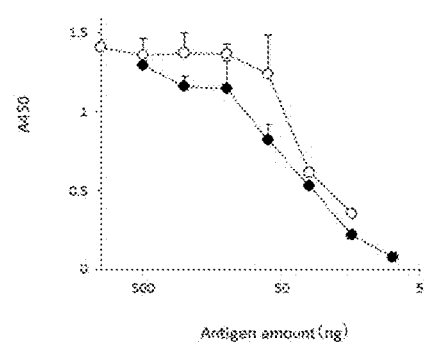

1. Immunogen Used in the Present Invention (1-1) With Regard to the Target Oligosaccharide Chain "CDw75" of the Present Invention The sugar chain structure of the target oligosaccharide chain "CDw75" of the present invention is represented by "6'-Sialyl-LacNAc (Siaα2,6Galβ1,4GlcNAc)" of the following general formula (1).

[Chemical Formula 2]

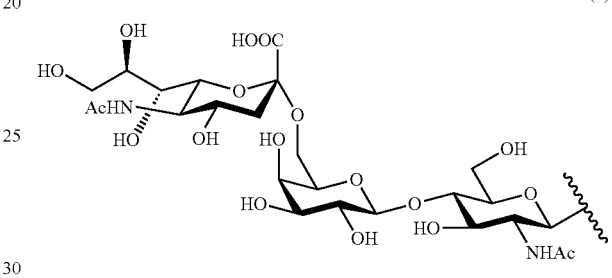

General formula (1)

To the naturally reducing terminal in which the sugar chain of interest is observed, proteins, lipids, carbohydrates or the like are bound. However, the anti-CDw75 antibody of the present invention recognizes only the sugar chain as a sugar chain epitope.

"CDw75" is one kind of sialylated sugar chains that are expressed in mammalian cells, and it gathers attention as a tumor marker (CDw75) which serves as a diagnosis indicator for malignancy determination of B-cell lymphoma, gastric cancer, or colorectal cancer and also as a molecular target for treatment of malignant tumor.

(1-2) Glycolipid Antigen (Immune Induction by Carrier Lipid Compound)

As a "CDw75" sugar chain antigen of the present invention, use is made of "CDw75-C12L" represented by the following general formula (2), which is a glycolipid antigen to which the carrier lipid compound "HOCH$_2$CH(NH—CO)—(CH$_2$)$_{22}$—CH$_3$)—(CH$_2$)$_9$—CH$_3$" (C12L) developed by the inventors of the present invention is bound.

[Chemical Formula 3]

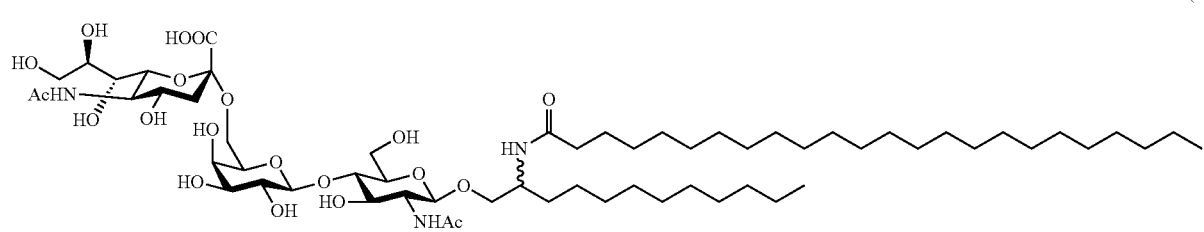

General formula (2)

(1-3) Method for Producing Glycolipid Antigen "CDw75-C12L"

As a method for conjugation of "C12L" of the carrier compound to the oligosaccharide chain "CDw75", it is possible that, while the hydroxyl groups other than the hydroxyl group added to the reducing terminal of "CDw75" are protected, "C12L" having the —OH group converted to an active group like a halogen group is subjected to a condensation reaction so that conjugation is achieved while maintaining the structure of "CDw75".

Further, the production can be made according to the following method, for example.

First, a sugar donor derived from N-acetylglucosamine (for example, 3,4,6-tri-O-acetyl-2-deoxy-2-(4,5-dichlorophthalimide)-D-glucopyranosyl bromide) is coupled to 2-azide alkyl alcohol $CH_3(CH_2)_9CH(N_3)CH_2OH$ as an acceptor by a glycosylation reaction. Then, by performing a deprotection reaction of the hydroxyl groups and reduction of the side chain azide group, a glucosamine derivative having an amino group, that is, $GlcNAc-CH_2CH(NH_2)(CH_2)_9CH_3$, is synthesized.

The above compound is subjected to an enzyme reaction, which uses β1,4-galactosyl transferase and α2,6-sialyl transferase, to yield a sialyl trisaccharide. Then, the side chain amino group and fatty acid (lignoceric acid) are condensed by an amidation reaction to synthesize CDw75-C12L.

2. With Regard to Monoclonal Antibody of the Present Invention

The monoclonal antibody of the present invention as described herein indicates a monoclonal antibody that is obtained by immunization using a glycolipid antigen in which "CDw75" sugar chain and the carrier lipid (C12L) are bound to each other.

The monoclonal antibody of the present invention is an antibody which recognizes only the "CDw75" sugar chain structure as a sugar chain epitope. By having very high specificity and affinity, it can fully function not only as a whole antibody but also as a fragment (for example, Fab or F(ab')$_2$ fragment). Accordingly, the monoclonal antibody of the present invention as described herein also means a functional fragment having "CDw75" sugar chain recognition ability. Both can be also described as an "anti-CDw75 monoclonal antibody or a fragment thereof."

Furthermore, the monoclonal antibody of the present invention may be either a humanized antibody or a human antibody. If the humanized antibody is a mouse-human chimeric antibody, for example, it can be produced by isolating the antibody gene from a mouse cell which produces the monoclonal antibody of the present invention, performing recombination of the constant region of H chain with the gene of the constant region of H chain of human immunoglobulin, and introducing the recombinant to a mouse myeloma cell. Furthermore, the human antibody can be also produced by immunizing a mouse of which immune system is replaced with that of a human with a glycolipid antigen in which the "CDw75" sugar chain and the carrier lipid (C12L) are bound to each other.

The monoclonal antibody of the present invention can be expressed as follows.

Anti-CDw75 monoclonal antibody which recognizes the sugar chain structure of "CDw75 (Siaα2,6Galβ1,4GlcNAc)" but does not recognize the sugar chain structure of "LacNAc (Galβ1,4GlcNAc)", "3'-Sialyl-LacNAc (Siaα2,3Galβ1,4GlcNAc)", and "6'-Sialyllactose (Siaα2,6Galβ1,4Glc)".

Herein, the anti-CDw75 monoclonal antibody of the present invention can be also used after being bound to a compound to which an oligosaccharide can bind, for example, a protein, a lipid, a sugar, a glycoprotein, or a glycolipid, a cell or a substrate, or a vehicle for immobilization.

Meanwhile, the "substrate" described herein means a substrate that is widely used for a sugar chain array or beads for purification. Polystyrene, PVDF, glass or the like is used as a substrate. Beads can be magnetic beads. It is desirable that the surface of a substrate is treated in advance to have high affinity for a molecule which has both hydrophobicity and hydrophilicity. Furthermore, as for the "vehicle for immobilization", a gelling material such as agarose, dextran, cellulose, starch, or polyacrylamide, which can be used as an affinity column or the like, is preferable.

3. Method for Producing Monoclonal Antibody of the Present Invention (3-1) Method for Immunization and Method for Screening Hybridoma As for the method for producing the monoclonal antibody of the present invention, a method well known in the pertinent can be employed (for example, Shepherd P. and Dean C., Monoclonal Antibodies, Oxford University Press, 2000).

Specifically, with regard to the "CDw75" sugar chain, a non-human mammalian like rat, mouse, or rabbit, preferably mouse, is immunized with an immunity inducing agent, that is, an artificial glycolipid antigen (CDw75-C12L) constructed of the carrier lipid compound (C12L) that is developed by the inventors of the present invention. For example, a liposome method by which liposome produced by dissolving in lipid such as cholesterol and phospholipids together with an adjuvant (Lipid-A) is administered by intravenous injection is preferably used (method by Brodin, et. al.; Eur. J. Immunol., 16, 951-956, 1986).

The administration amount of a fused sugar chain antigen per animal is 0.05 to 0.2 mg with use of an adjuvant. As for the adjuvant, *Salmonella minnesota* strain R595 treated with an acid, complete Freund adjuvant, or the like can be used. However, the liposome method containing Lipid-A is preferable. At that time, additional immunization can be performed. The immunization is generally performed by intravenous, subcutaneous, or intraperitoneal injection. Furthermore, the immunization interval is not particularly limited, and the immunization is generally performed 1 to 10 times, preferably 3 to 6 times, with an interval of several days to several weeks, preferably 2 to 5 weeks. In addition, the antibody-producing cells are collected 1 to 7 days, and preferably 2 to 3 days after the last immunization day. Examples of the antibody-producing cells include a spleen cell, a lymph node cell, and a peripheral blood cell. It is preferably a spleen cell or a local lymph node cell.

(3-2) Method for Selecting Hybridoma

According to a common method, spleen cells are fused to myeloma cells, and after incubation in a medium with thymus gland feeder cells in the presence of IL-6, selection by using HAT in IMDM medium is performed. Subsequently, the supernatant of amplifying clones is screened by using the "CDw75" sugar chain. At that time, although immunohistochemical analysis or the like can be used, a simple screening method based on enzyme-linked immunosorbent assay (ELISA or the like) or Western blot can be applied to the "CDw75" sugar chain which has been immobilized on a substrate. Application of ELISA or Western blot for selecting a hybridoma which produces the "CDw75" sugar chain antibody is also a merit of the present invention.

In the present invention, the antibody titer in the culture supernatant is preferably evaluated by ELISA, and the hybridoma is selected by using the antibody titer as a reference. For example, the antibody titer is evaluated in terms of activity of a peroxidase, which is a labeling enzyme of anti-mouse immunoglobulin antibody used as a secondary antibody. As a chromogenic substrate of peroxidase, TMB is used. According to addition of 2 N sulfuric acid after the reaction, the absorbance intensity at 450 nm is evaluated.

First, a hybridoma cell which produces a monoclonal antibody recognizing the glycolipid antigen "CDw75-C12L" and the glycoprotein (Fetuin) having CDw75 (6'-Sialyl-LacNAc) sugar chain structure as an immunogen is selected, and subsequently, a hybridoma which produces a monoclonal antibody having no reactivity to "LacNAc" as a precursor and the sugar chain structure of "3'-Sialyl-LacNAc", which has a structure most similar to the target oligosaccharide chain among sugar chains present in mammalian body, is selected.

(3-3) Deposition of Hybridoma of the Present Invention

Among the hybridomas obtained from Examples of the present invention, the hybridoma FR9 producing the monoclonal antibody FR9 with the highest specificity and affinity was deposited with NITE Patent Microorganisms Depositary on Jan. 21, 2013. After given with the "Deposit number: NITE P-1516" on Mar. 13, 2013, it was transferred on Apr. 15, 2014 as international deposition under the number of "NITE BP-01516".

The monoclonal antibody FR9 can be easily obtained from the hybridoma by a common cell culture method or an ascites fluid forming method.

The term of deposit is a term of at least thirty (30) years and at least five (5) years after the most recent request for the furnishing of a sample of the deposit was received by the depository. The samples will be stored under agreements that would make them available beyond the enforceable life of the patent for which the deposit was made. The biological material is capable of self-replication and was viable at the time of deposit, and will be viable during the term of deposit. Access to the deposit will be available during pendency of the patent application to one determined by the Director to be entitled thereto under §1.14 and 35 U.S.C. 122. All restrictions imposed by the depositor on the availability to the public of the deposited material will be irrevocably removed upon the granting of the patent.

4. Characteristics of Anti-CDw75 Antibody of the Present Invention (4-1) Sugar Chain Structure Recognition Specificity of Anti-CDw75 Antibody The anti-CDw75 antibody of the present invention recognizes sugar chain structure "CDw75" as a sugar chain epitope.

Although it can recognize the glycolipid antigen "CDw75-C12L" and the glycoprotein (Fetuin) containing CDw75 (6'-Sialyl-LacNAc) sugar chain structure as an immunogen, it does not recognize "LacNAc" as a precursor and the sugar chain structure of "3'-Sialyl-LacNAc, which has a structure most similar to the target oligosaccharide chain among sugar chains present in mammalian body, even when they are in the form of a glycolipid or glycoprotein. Furthermore, it also has high recognition specificity of not recognizing the oligosaccharide chain "6'-Sialyllactose (Siaα2,6Galβ1,4Glc)" with similar structure.

According to Examples of the present invention, confirmation was made according to the following method.

Figure 2:
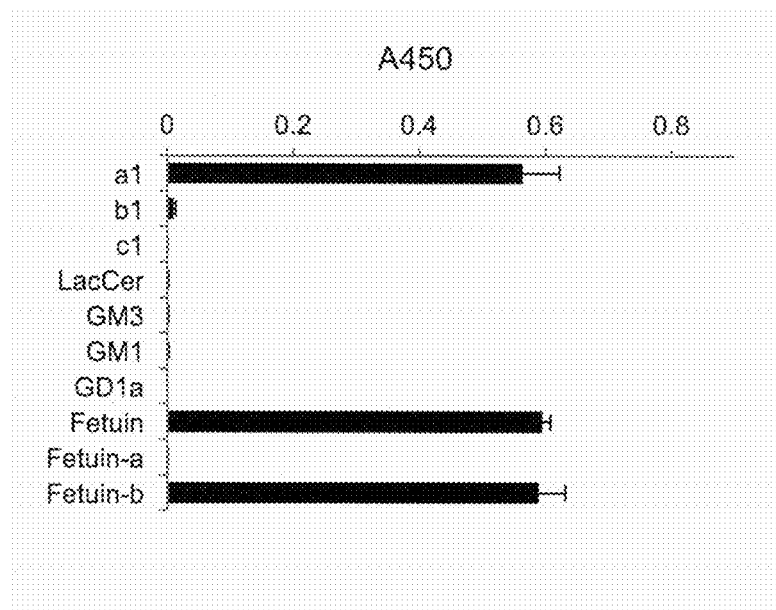
FIG. 2 shows ELISA-based analysis of specificity of the developed monoclonal antibody FR9. With regard to the antigen recognition specificity of the FR9 antibody, ELISA-based analysis was made using various sugar chain antigen compounds that are described in Table 1.

Together with "CDw75 (Siaα2,6Galβ1,4GlcNAc)", a compound having a pseudo sugar chain like "LacNAc (Galβ1,4GlcNAc)" and "3'-Sialyl-LacNAc (Siaα2,3Galβ1,4GlcNAc)" is immobilized on a substrate (ELISA plate) by evaporation and solidification, and the antibody titer (absorbance intensity at 450 nm) was evaluated by ELISA (FIG. 2). The compounds used for immobilization are shown below (Table 1). In the table, CerA represents a ceramide derivative (HOCH$_2$CH(NH—CO—(CH$_2$)$_{16}$—CH$_3$)—(CH$_2$)$_9$—CH$_3$) in which bonding to reducing terminal of each sugar chain is formed via a hydroxyl group. Cer is ceramide (natural form), and LacCer, GM3, GM1, and GD1a are glycolipids of a natural form having sugar chains bound to each ceramide. R represents the main structure of Fetuin (Fetuin sugar chain constituting the reducing side of sugar chain structure shown in the table and the core protein).

TABLE 1

| Antigen | Structure |
|---|---|
| a1 | Siaα2,6Galβ1,4GlcNAcβ1-CerA |
| b1 | Siaα2,3Galβ1,4GlcNAcβ1-CerA |
| c1 | Galβ1,4GlcNAcβ1-CerA |
| LacCer | Galβ1,4Glcβ1-Cer |
| GM3 | Siaα2,3Galβ1,4Glcβ1-Cer |
| GM1 | Galβ1,3GalNAcβ1,4(Siaα2,3)Galβ1,4Glcβ1-Cer |
| GD1a | Siaα2,3Galβ1,3GalNAcβ1,4(Siaα2,3)Galβ1,4Glcβ1-Cer |
| Fetuin | Siaα2,6(3)Galβ1,4GlcNAcβ1-R |
|  | Siaα2,3Galβ1,3GalNAcα1-R |
|  | Siaα2,3Galβ1,3(Siaα2,6)GalNAcα1-R |
| Fetuin-a | Galβ1,4GlcNAcβ1-R |
|  | Galβ1,3GalNAcα1-R |
| Fetuin-b | Siaα2,6Galβ1,4GlcNAcβ1-R |
|  | Galβ1,4GlcNAcβ1-R |
|  | Siaα2,3Galβ1,3GalNAcα1-R |
|  | Siaα2,3Galβ1,3(Siaα2,6)GalNAcα1-R |

From the results, it was confirmed that the antibody titer is clearly present against the target CDw75 sugar chain while no antibody titer is present against a sugar chain other than the CDw75. Furthermore, since the glycoprotein Fetuin contains, as a sugar chain structure, "3'-Sialyl-LacNAc (Siaα2,3Galβ1,4GlcNAc)" as well as "CDw75 (Siaα2,6Galβ1,4GlcNAc)", by confirming the prominent antibody titer against Fetuin, the absence of antibody titer against Fetuin (Fetuin-a) from which sialic acid is removed by digestion with sialidase, and no change in the antibody titer against Fetuin (Fetuin-b) from which "3'-Sialyl-LacNAc" is selectively removed by α2,3 sialidase, it was able to confirm that the anti-CDw75 antibody has selective recognition specificity for CDw75.

For comparison, the recognition specificity for the sugar chain structure by commercially available anti-CDw75 antibody (LN-1) was also evaluated in the same manner as above. The result was below the detection limit for any of the above antigens (data not shown).

Figure 3:
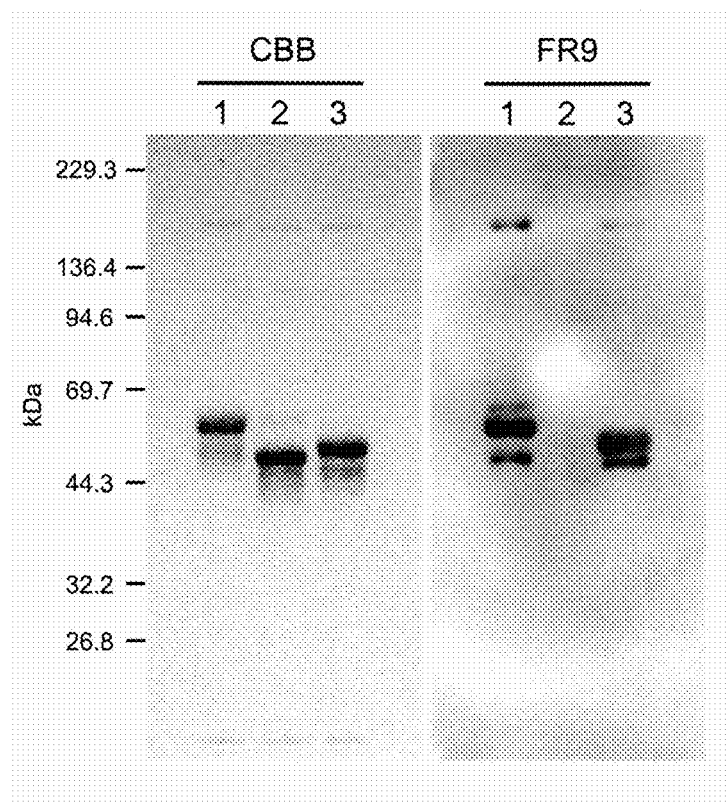
FIG. 3 shows specificity analysis of the monoclonal antibody FR9 by Western blot. Applicability of the FR9 antibody on Western blot was evaluated. The drawing on the left column represents the CBB staining image of the Fetuin glycoprotein which has been used, and the drawing on the right column represents the Western blot image. 1: Fetuin glycoprotein, 2: Fetuin glycoprotein (Fetuin-a) obtained after enzyme hydrolysis of all sialic acids, 3: Fetuin glycoprotein (Fetuin-b) obtained after selective enzyme hydrolysis of α2,3 linked sialic acid.

Similarly, the selective recognition specificity for CDw75 was also confirmed by Western blot analysis using the aforementioned glycoprotein Fetuin, Fetuin-a, or Fetuin-b (FIG. 3).

In addition to above, it is also possible to have brief confirmation by using the commercially available "Sugar chain array."

Figure 4:
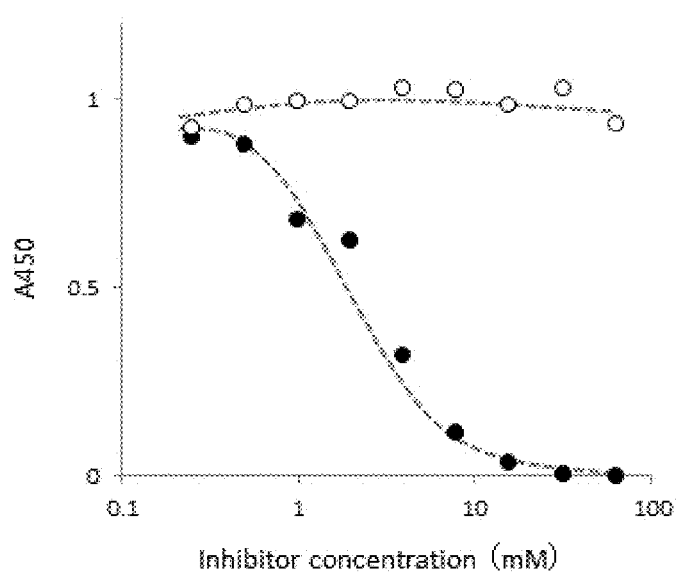
FIG. 4 shows specificity analysis of the monoclonal antibody FR9 based on competitive inhibition assay. The affinity of the FR9 antibody for sialyl lactose (Siaα2,6Galβ1,4Glc) was analyzed by competitive inhibition assay. After adding sialyl lactose (empty circle) or CDw75 oligosaccharide chain (filled circle) as a competitive agent, their influence was evaluated by ELISA. On the x axis, concentration of the competitive agent added was plotted, and on the y axis, the binding amount of the FR9 antibody was plotted.

Furthermore, in order to determine the level of the recognition specificity of the anti-CDw75 antibody (FR9 antibody) of the present invention, 6'-Sialyllactose having a sugar chain structure that is very close to CDw75 was examined based on a competitive inhibition assay using immobilized Fetuin (FIG. 4). As a result, it was found that the reaction between the FR9 antibody and Fetuin is inhibited according to addition of the CDw75 sugar chain but not by the addition of 6'-Sialyllactose. Thus, it was confirmed that 6'-Sialyllactose does not react with the FR9 antibody.

Figure 5:
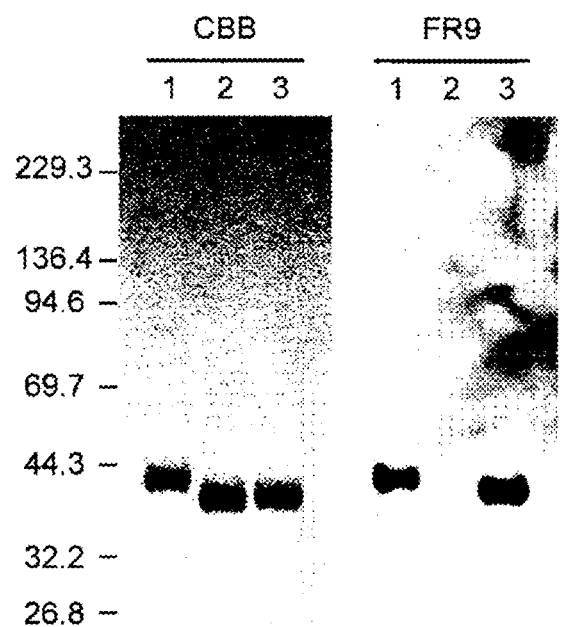
FIG. 5 shows specificity analysis 2 of the monoclonal antibody FR9 based on Western blot. Applicability of the FR9 antibody on Western blot was evaluated. The drawing on the left column represents the CBB staining image of the al-acidic glycoprotein (AGP) which has been used, and the drawing on the right column represents the Western blot image. 1: AGP, 2: AGP (AGP-a) obtained after enzyme hydrolysis of all sialic acids, 3: AGP (AGP-b) obtained after selective enzyme hydrolysis of α2,3 linked sialic acid.

Furthermore, according to Western blot analysis using AGP glycoprotein, it was confirmed that the anti-CDw75 antibody (FR9 antibody) of the present invention exhibits the same reactivity as Fetuin even when the CDw75 sugar chain is included in a glycoprotein other than the Fetuin glycoprotein, and also the reactivity has selective recognition specificity (FIG. 5). Herein, since AGP glycoprotein includes "3'-Sialyl-LacNAc (Siaα2,3Galβ1,4GlcNAc)" with "CDw75 (Siaα2,6Galβ1,4GlcNAc)" as a sugar chain structure like the Fetuin glycoprotein, the antibody titer observed for AGP is absent for the AGP (AGP-a) from which sialic acid has been removed. It was also confirmed that the antibody titer did not change for the AGP (AGP-b) from which the "3'-Sialyl-LacNAc" structure has been selectively removed. Main sugar chain structures of AGP, AGP-a, and AGP-b are shown in Table 2. R represents the main structure of AGP (AGP sugar chain constituting the reducing side of sugar chain structure shown in the table and the core protein).

TABLE 2

| Antigen | Structure |
|---|---|
| AGP | Siaα2,6(3)Galβ1,4GlcNAcβ1-R |
|  | Galβ1,4(Fucα1,3)GlcNAcβ1-R |
| AGP-a | Galβ1,4GlcNAcβ1-R |
|  | Galβ1,4(Fucα1,3)GlcNAcβ1-R |
| AGP-b | Siaα2,6Galβ1,4GlcNAcβ1-R |
|  | Galβ1,4GlcNAcβ1-R |
|  | Galβ1,4(Fucα1,3)GlcNAcβ1-R |

(4-2) With Regard to Having High Affinity

Affinity (dissociation constant: Kd value) of the anti-CDw75 antibody (FR9 antibody) for Fetuin was determined by a calculation method which is based on ELISA (Friguet B., et al., J. Immunol. Methods, 77, 305-319, 1985). The antibody was diluted to concentration of $1 \times 10^{-7}$ M using PBS or the like, and by mixing and incubating Fetuin which has been serially diluted to have concentration of from 25 to $1.56 \times 10^{-7}$ M, an antigen antibody complex was formed. The amount of free antibody in the mixture was calculated by ELISA in which Fetuin (1 μg) was used as an immobilized antigen. From the obtained result, Kd value was determined using Scatchard plot (FIG. 1A). The calculated Kd value was $8.86 \times 10^{-7}$ M, and considering that the Kd value of an antibody or lectin binding to a sugar chain is generally $1 \times 10^{-3}$ to $1 \times 10^{-6}$ M, the developed anti-CDw75 antibody was found to have high affinity.

Same calculation as the above was tried to have Kd value of the commercially available LN-1 antibody. However, the antibody reaction of LN-1, which has a glycolipid or a glycoprotein containing CDw75 as an antigen, showed a result below the detection limit of ELISA (data not shown).

Furthermore, based on ELISA in which a plate immobilized with serially diluted Fetuin and CDw75-C12L is used, the limit amount of the antigen that can be detected by the produced antibody was determined (FIG. 1B).

Figure 6:
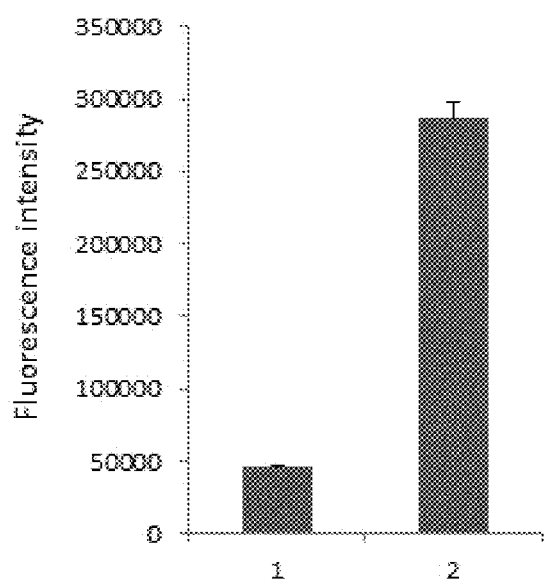
FIG. 6 shows detection of CDw75 expressed on surface layer of cancer cell (B-cell lymphoma cell). By using the FR9 antibody, CDw75 expressed on a cell surface layer of B-cell lymphoma cell (Burkitt lymphoma cell line: Raji cell) was detected. 1: Negative control, 2: FR9 antibody.

(4-3) With Regard to Possibility of Detecting CDw75 Present on Surface Layer of Cancer Cell The CDw75 sugar chain is expressed, in the form of glycoprotein or glycolipid, as an antigen present on a cell surface layer, and the antigen present on a cell surface layer is a molecular target for cell diagnosis or malignant tumor. The reaction between the FR9 antibody and the CDw75 on a cell surface layer was confirmed by a cytofluorometric assay. Highly malignant B-cell lymphoma cell (Burkitt lymphoma cell line: Raji cell) expressing CDw75 was incubated with the FR9 antibody, and then the antibody reaction was labeled with a fluorescent-labeled secondary antibody followed by detection using a fluorescence detector (FIG. 6). Compared to a negative control in which the FR9 antibody has not been added, a clear increase in fluorescence was detected. As such, it was found that the FR9 antibody reacts with CDw75 on surface layer of Raji cell.

5. Application of Anti-CDw75 Antibody of the Present Invention (5-1) Pharmaceutical Composition Containing Anti-CDw75 Monoclonal Antibody of the Present Invention as Effective Component The anti-CDw75 monoclonal antibody of the present invention can be used as an antibody pharmaceutical which has, as a target, the sugar chain antigen "CDw75" widely expressed on a cell surface of progressed B-cell lymphoma, gastric cancer, and/or colorectal cancer (Non Patent Literature 3). Namely, it can be used as an effective component of a pharmaceutical composition for inhibiting and/or treating B-cell lymphoma, gastric cancer, or colorectal cancer.

Furthermore, as the "CDw75" sugar chain is present on human bronchial epithelial cell and serves as a main infection receptor for human influenza virus (Non Patent Literature 1), when administered, the anti-CDw75 monoclonal antibody of the present invention can function as a competitive inhibitor for human influenza virus. Namely, since the anti-CDw75 monoclonal antibody of the present invention can be used as an antibody pharmaceutical having influenza virus infection receptor as a target, it can be used as an effective component of a pharmaceutical composition for preventing and/or treating influenza.

When the anti-CDw75 monoclonal antibody of the present invention is prepared as an antibody pharmaceutic composition for gastric cancer or colorectal cancer, it is possible to use it as a conjugate in which an anticancer agent such as cyclophosphamide, fluorouracil, doxifluridin, paclitaxel, levofolinate, methotrexate, irinotecan, cisplatin, carboplatin, or oxaliplatin is linked to the antibody. It can be also used in combination with other anticancer agent for gastric cancer or colorectal cancer. When it is used as an antibody pharmaceutical composition for influenza, a conjugate in which a neuraminidase inhibitor such as oseltamivir or zanamivir is linked to the antibody can be used, and it can be also used in combination with other agent for treating influenza.

In the pharmaceutical composition of the present invention, if necessary, a pharmaceutically acceptable carrier (a vehicle, a diluent, a stabilizer, a preservative, a buffering agent, an emulsifier, or other additives) can be additionally included in addition to the monoclonal antibody of the present invention. The pharmaceutical composition can be prepared as a composition in the form of tablet, powder, injection solution, capsule, emulsion, or syrup, and it can be administered either orally or parenterally. The administration amount depends on the severeness of symptoms, age, body weight or the like of a patient, or an administration method and, in terms of the weight of an antibody as an effective component, it is generally in the range of about 10 ng to about 100 mg/kg of body weight. The therapeutic agent for gastric cancer and/or colorectal cancer is preferably an injection solution, and it can be prepared by, for example, dissolving or suspending in a non-toxic and pharmaceutically acceptable carrier like physiological saline or commercially available distilled water for injection to have concentration of 0.1 µg of antibody/ml of carrier to 10 mg of antibody/ml of carrier.

(5-2) Method for Detecting or Method for Quantifying "CDw75" Sugar Chain Using Anti-CDw75 Monoclonal Antibody of the Present Invention By using the anti-CDw75 monoclonal antibody of the present invention, the amount of "CDw75" sugar chain epitope present in a sample can be detected with high sensitivity and also with precise quantification.

Specifically, by contacting a sample from a subject with the anti-CDw75 monoclonal antibody of the present invention, the amount of the "CDw75" sugar chain epitope present in the sample is measured.

With regard to a method for detecting qualitatively or quantitatively the presence of the "CDw75" sugar chain epitope in a sample by using the monoclonal antibody of the present invention, enzyme immunoassay (EIA) like sandwich ELISA, radioactive immunoassay (RIA), immunochromatography, or Western blot can be used. Those techniques are well known to a person skilled in the art.

(5-3) Method for Determining and Diagnosing Morbidity or Tumor Malignancy of B-Cell Lymphoma, Gastric Cancer, or Colorectal Cancer by Using Anti-CDw75 Monoclonal Antibody of the Present Invention, and Kit Therefor If the "CDw75" sugar chain is detected and/or quantified by using the anti-CDw75 monoclonal antibody of the present invention, not only an occurrence of B-cell lymphoma, gastric cancer, or colorectal cancer in a subject can be determined but also malignancy of tumor in a patient with gastric cancer, or colorectal cancer can be determined.

Namely, the anti-CDw75 monoclonal antibody of the present invention can be used for a method for detecting, a method for determining, or a method for diagnosing malignancy of tumor in B-cell lymphoma, gastric cancer, or colorectal cancer, and it can be also used for a detection kit, a determination kit, or a diagnostic kit therefor. For such case, a pharmaceutically acceptable carrier, vehicle, diluent, or the like can be appropriately included, if necessary.

For determining and diagnosing morbidity or tumor malignancy of gastric cancer, or colorectal cancer, a sample from a subject is contacted with the monoclonal antibody of the present invention to measure the amount of the "CDw75" sugar chain epitope present in the sample. Accordingly, an occurrence of gastric cancer or colorectal cancer can be determined and also the malignancy of the gastric cancer or colorectal cancer can be determined. At that time, by establishing in advance a calibration curve based on the value of the "CDw75" sugar chain epitope amount which is measured from a sample from a patient with gastric cancer, or colorectal cancer with known malignancy and from a sample of stomach ulcer or benign tumor and/or normal sample, more precise determination can be made. In addition, by using a known monoclonal antibody for detecting gastric cancer or colorectal cancer marker, lectin, or the like in combination, precision of the detection can be improved.

(5-4) Purification of Compound Containing "CDw75" Sugar Chain or Cells Having "CDw75" Sugar Chain Antigen on Cell Surface When purification of a compound containing "CDw75" sugar chain or cells having "CDw75" sugar chain antigen on a cell surface is performed, the anti-CDw75 monoclonal antibody of the present invention is linked to a column carrier consisting of agarose or cellulose via an antibody binding protein such as Protein A or Protein G, or a cross linker such as a water soluble carbodiimide (WSC) or glutaraldehyde to prepare an affinity column, and a sample containing sugar chain is passed through the column. After the pass-through, the adsorbed compound containing "CDw75" sugar chain or cells having "CDw75" sugar chain antigen on a cell surface are recovered.

It is also possible that adsorption is achieved by using beads (magnetic beads) in which the anti-CDw75 monoclonal antibody is linked via an antibody binding protein such as Protein A or Protein G, or a cross linker such as a water soluble carbodiimide (WSC) or glutaraldehyde.

EXAMPLES

Hereinbelow, the present invention is specifically described in view of the examples, but the present invention is not limited to them.

As described herein, other terms and concept are based on the meaning of terms that is generally employed in the pertinent art, and various techniques used for carrying out the present invention can be easily and surely performed by a skilled person in the art based on known literatures or the like, except the techniques that are specifically described with their origin. Furthermore, various analyses or the like were performed based methods described in manuals or catalogues of an analytical instrument, a reagent, or a kit that are used.

Meanwhile, the context described in technical literatures, patent documents, and specifications of patent applications cited in the present invention are incorporated herein by reference.

(Example 1) Preparation of Glycolipid Antigen "CDw75-C12L"

3,4,6-Tri-O-acetyl-2-deoxy-2-(4,5-dichlorophthalimide)-D-glucopyranosyl bromide (Shimizu H et al., Biosci. Biotech. Biochem., 60, 73-76, 1996) as a sugar donor derived from N-acetylglucosamine was coupled to 2-azide alkyl alcohol $CH_3(CH_2)_9CH(N_3)CH_2OH$ as an acceptor by glycosylation reaction followed by deprotection of hydroxyl group and reduction of side azide group to synthesize a glucosamine derivative having an amino group, GlcNAc-$CH_2CH(NH_2)$ $(CH_2)_9CH_3$.

Reaction scheme (1)

[Chemical Formula 4]

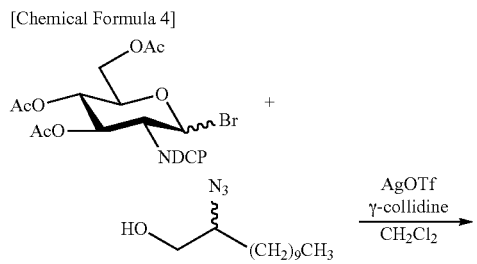

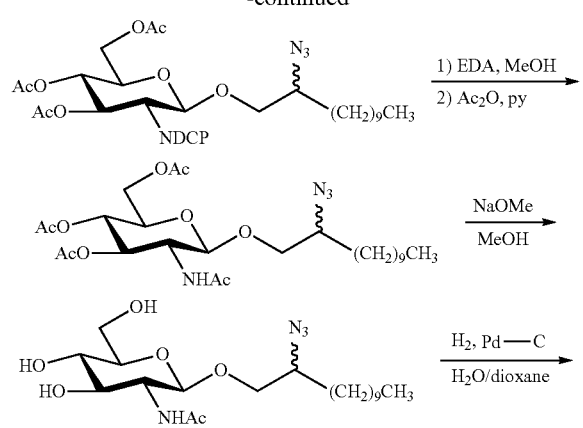

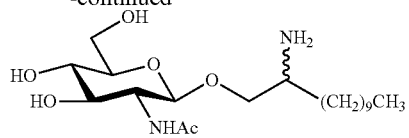

The obtained intermediate compound was subjected to an enzyme reaction using β1,4-galactosyl transferase according to the following reaction scheme (2), and then the sugar chain was extended to have transformation into LacNAc-$CH_2CH(NH_2)(CH_2)_9CH_3$. It was further subjected to an enzyme reaction using α2,6-sialyl transferase to yield a sialyl trisaccharide. Subsequently, the side amino group of 6'-Sialyl-LacNAc-$CH_2CH(NH_2)(CH_2)_9CH_3$ and lignoceric acid were condensed by an amidation reaction to synthesize "CDw75-C12L" that is represented by the following general formula (2).

Reaction scheme (2)

[Chemical Formula 5]

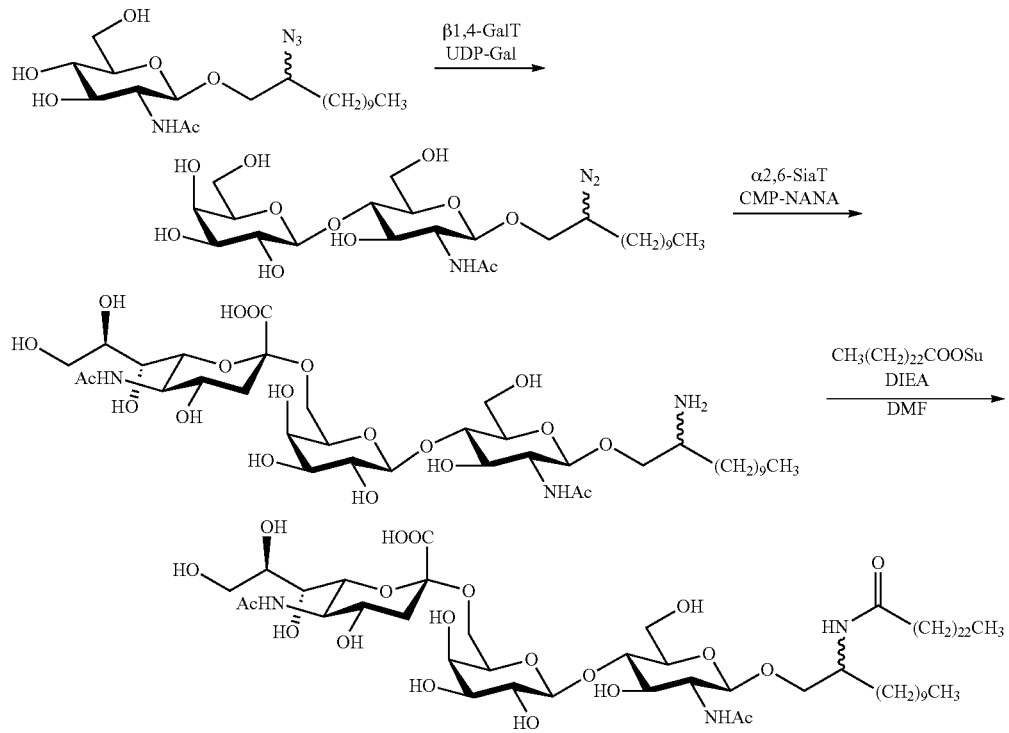

[Chemical Formula 6]

General formula (2)

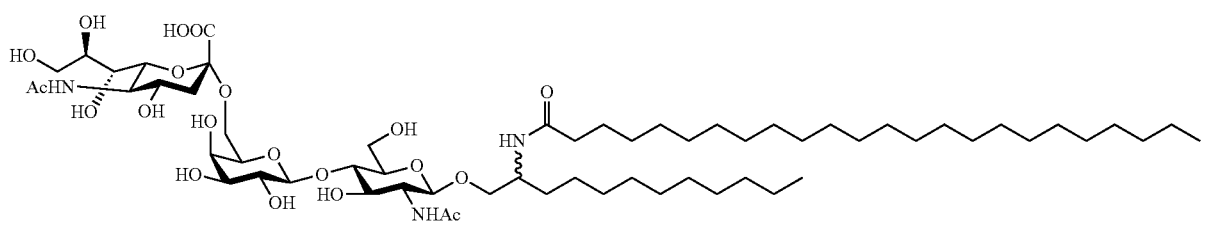

"CDw75-C12L" was purified by normal phase silica gel column chromatography (ethyl acetate:ethanol:water=6:2:1), and according to $^1$H-NMR spectroscopy and mass analysis based on MALDI-TOF, it was confirmed to have the above-described structure.

(Example 2) Preparation of Hybridoma Producing Anti-CDw75 Monoclonal Antibody

According to a liposome method (method by Brodin et al.; Eur. J. Immunol., 16, 951-956, 1986), 100 μg of the glycolipid antigen "CDw75-C12L" were admixed with phospholipid, cholesterol, and Lipid-A in methanol solution, and after evaporation and dissolving in PBS buffer at 50° C., a liposome was formed. By using the liposome as an immunogen, a mouse (C3H/HeN strain) was immunized.

Immunization with the immunogen was performed subcutaneously, four times with an interval of 2 weeks. Two weeks later, abdominal immunization was performed, and spleen cells were collected three days thereafter. According to cell fusion with myeloma cell Sp1 strain, a hybridoma cell was prepared.

First, from the hybridoma cells which have been cultured in 8 plates with 96 wells so as to have one colony/well (768 wells in total), the culture supernatant was collected in an amount of 0.05 ml for each, and by having the absorbance of 0.1 or more at 450 nm according to ELISA as a reference antibody titer, hybridoma cells which produce a monoclonal antibody recognizing the glycoprotein (Fetuin) containing the 6'-Sialyl-LacNAc (CDw75) sugar chain structure were selected. As a result, positive clones were obtained from 131 wells (appearance ratio of 17.1%).

The antibody titer in the culture supernatant was estimated by ELISA, and the antibody titer (absorbance) was evaluated in terms of the activity of peroxidase, which is a labeling enzyme for an anti-mouse immunoglobulin antibody used as a secondary antibody. As a chromogenic substrate for peroxidase, TMB was used. According to addition of 2 N sulfuric acid after the reaction, the absorbance intensity at 450 nm was evaluated.

Subsequently, 40 hybridoma cells which produce a monoclonal antibody recognizing the glycolipid antigen "CDw75-C12L" as an immunogen were selected, and two hybridoma cells producing a monoclonal antibody with no reactivity for "LacNAc" as a precursor and the glycolipid (Table 1, b1, c1) and glycoprotein (Fetuin-a), which have a sugar chain structure of "3'-Sialyl-LacNAc" with a structure most similar to the target oligosaccharide chain among sugar chains present in mammalian body, were selected.

Any one of the monoclonal antibodies obtained from those hybridomas is an anti-CDw75 monoclonal antibody which has high specificity for the "CDw75" sugar chain structure, and it corresponds to the anti-CDw75 monoclonal antibody of the present invention.

Among those two hybridomas, the "hybridoma FR9", which produces anti-CDw75 monoclonal antibody exhibiting the highest antibody titer and excellent specificity and affinity, was deposited with NITE Patent Microorganisms Depository on Jan. 21, 2013. After given with the "Deposit number: NITE P-1516" on Mar. 13, 2013, it was transferred on Apr. 15, 2014 as international deposition under the number of "NITE BP-01516".

(Example 3) Evaluation of Monoclonal Antibody Produced by Hybridoma FR9

(3-1) Affinity for CDw75

With regard to the affinity of the monoclonal antibody included in the culture supernatant of FR9 cells (hereinbelow, also referred to as "FR9 antibody") for CDw75, an evaluation was made by determining the dissociation constant (Kd value) having CDw75-containing Fetuin as an antigen. As a result, the Kd value was found to be $8.86 \times 10^{-7}$ M. Since the Kd value of an antibody or lectin binding to a sugar chain is generally $1 \times 10^{-3}$ to $1 \times 10^{-6}$ M, the developed antibody was found to have high affinity for the CDw75 sugar chain (FIG. 1A).

For comparison, same calculation as the above was tried to obtain a Kd value of the commercially available anti CDw75 antibody (LN-1). However, the antibody reaction of LN-1, which has a glycolipid or a glycoprotein containing CDw75 as an antigen, showed a result below the detection limit of ELISA, and thus it was confirmed to be an antibody having extremely low affinity for the CDw75 sugar chain itself (data not shown).

According to the result of measuring detection limit of Fetuin and CDw75-C12L by ELISA, an extremely small amount of Fetuin (about 15 ng) can be detected by the FR9 antibody (FIG. 1B).

(3-2) Antigen Recognition Specificity of FR9 Antibody (ELISA)

Next, the antigen recognition specificity of FR9 antibody was evaluated by ELISA (FIG. 2). Sugar chain structure of the antigen used is as described above (Table 1). Since the FR9 antibody strictly recognizes as an epitope the glycolipid or glycoprotein having CDw75 structure as an antigen and does not react with 3'-Sialyl-LacNAc structure with a similar structure or LacNAc structure as a precursor, the developed antibody has high specificity for the CDw75 sugar chain.

For comparison, the anti CDw75 antibody (LN-1) was evaluated with regard to the sugar chain structure recognition specificity, in the same manner as above. However, the result was below the detection limit for any antigen, and it was found to be an antibody which has low recognizability for the CDw75 sugar chain structure itself (data not shown).

It was also confirmed according to the competitive inhibition assay (FIG. 4) that the FR9 antibody does not react with 6'-Sialyllactose. Specifically, to the FR9 antibody, CDw75 and 6'-Sialyllactose were added in advance as a competitive agent followed by incubation, and a reaction with a 96 well plate to which Fetuin (1 μg) has been immobilized was allowed to occur. Thereafter, the reaction between the FR9 antibody and Fetuin was evaluated by ELISA. As a result, it was found that the binding reaction between the FR9 antibody and the Fetuin glycoprotein is inhibited in concentration dependent manner when the CDw75 oligosaccharide chain is added as a competitive agent. However, 6'-Sialyllactose did not inhibit the reaction even when it was added in an amount that is 100 times the CDw75. This result demonstrates that the FR9 antibody does not react with 6'-Sialyllactose having a structure that is very similar to CDw75. Thus, it was confirmed that the developed antibody has very high specificity for the CDw75 sugar chain.

(3-3) Antigen Recognition Specificity of FR9 Antibody (Western Blot)

Subsequently, applicability of the FR9 antibody for Western blot generally used for detecting a specific protein was determined (FIG. 3).

The Fetuin glycoprotein having the CDw75 (6'-Sialyl-LacNAc) structure as an antigen was treated with two kinds of sialidase and specificity analysis was also performed. As a result, it was found that the FR9 antibody can detect the Fetuin glycoprotein but does not react with the glycoprotein of which CDw75 sugar chain is removed by an enzyme reaction. Meanwhile, it reacts, at the same level as non-treated Fetuin, with the Fetuin glycoprotein of which 3'-Sialyl-LacNAc sugar chain has been selectively removed.

Based on the results described above, it was confirmed that the developed anti-CDw75 antibody is an antibody having broad applicability which allows detection of CDw75 sugar chain with high specificity and high detection sensitivity even when it is used for Western blot.

It was also confirmed by Western blot using AGP as an antigen that, even for a different glycoprotein, reactivity of the FR9 antibody to CDw75 sugar chain contained in a glycoprotein is still shown (FIG. 5). Like the Fetuin glycoprotein, the AGP protein contains "CDw75 (Siaα2,6Galβ1,4GlcNAc)" and "3'-Sialyl-LacNAc (Siaα2,3Galβ1,4GlcNAc)" as a sugar chain structure (Table 2). Accordingly, together with the AGP glycoprotein, the FR9 antibody of the present invention is used for the reaction with each of AGP (AGP-a) in which the CDw75 structure is selectively removed from AGP by sialidase digestion and AGP (AGP-b) in which "3'-Sialyl-LacNAc" structure is selectively removed by α2,3 sialidase digestion. The FR9 antibody was able to detect the AGP glycoprotein, but it did not react with the protein of which CDw75 sugar chain has been removed by an enzyme reaction. Meanwhile, it reacts, at the same level as non-treated Fetuin, with the AGP glycoprotein of which 3'-Sialyl-LacNAc sugar chain has been selectively removed (FIG. 5).

Based on the results described above, it was confirmed that the anti-CDw75 antibody of the present invention can be used for detection of any glycoprotein containing CDw75, and it was found to be an antibody having broad applicability which allows detection of CDw75 sugar chain with high specificity and high detection sensitivity even when it is used for Western blot.

Furthermore, the anti-CDw75 antibody of the present invention is an antibody with high specificity which recognizes in very strict manner the sugar chain structure CDw75 represented by Siaα2,6Galβ1,4GlcNAc. When it is expressed in terms of cross reactivity, it can be described as an "anti-CDw75 monoclonal antibody which recognizes the sugar chain structure represented by Siaα2,6Galβ1,4GlcNAc but does not recognize the sugar chain structure represented by Galβ1,4GlcNAc, Siaα2,3Galβ1,4GlcNAc and 6'-Sialyllactose (Siaα2,6Galβ1,4Glc)."

(3-4) Antigen Recognition Specificity of FR9 Antibody (Cytofluorometric Assay)

Next, detection of CDw75 expressed on a cell surface layer was determined by a cytofluorometric assay. Since the antigen present on a cell surface layer is a molecular target for cell diagnosis or malignant tumor, if there is a reaction occurring between the FR9 antibody and the CDw75 on a cell surface layer, it can be applied for diagnosis or therapeutic agent. Highly malignant B-cell lymphoma cell (Burkitt lymphoma cell line: Raji cell) expressing CDw75 was labeled with the FR9 antibody and a fluorescent-labeled secondary antibody followed by detection using a fluorescence detector. As a result, compared to a negative control in which the FR9 antibody has not been added, a clear increase in fluorescence was detected. Based on the results, it was found that the FR9 antibody reacts with CDw75 on surface layer of Raji cell (FIG. 6).

(3-5) Comparison with Monoclonal Antibody Recognizing CDw75 Sugar Chain Antigen Described in Citation List (Non Patent Literature 6)

Also from Citation List (Non Patent Literature 6), a monoclonal antibody (241-5-2 antibody) which recognizes the anti-CDw75 sugar chain antigen has been obtained. Thus, it was compared to the result obtained from the FR9 antibody of the present invention, in terms of the specificity and affinity.

According to the descriptions of Non Patent Literature 6, the obtained 241-5-2 antibody reacts with the Fetuin glycoprotein containing the CDw75 sugar chain, but the epitope recognized by the 241-5-2 antibody was believed to be "Siaα2,6 structure", which is a partial structure of the CDw75 sugar chain "6'-Sialyl-LacNAc (Siaα2,6Galβ1,4GlcNAc)" (page 303 of Non Patent Literature 6). Namely, it cannot be said that the 241-5-2 antibody is a CDw75 sugar chain-specific antibody, and it reacts with any sugar chain having "Siaα2,6 structure".

On the other hand, the FR9 antibody of the present invention is an antibody which can recognize even a micro structure of the CDw75 sugar chain, and its epitope is the "6'-Sialyl-LacNAc (Siaα2,6Galβ1,4GlcNAc)" of entire length including not only the Siaα2,6 structure but also the GlcNAc structure of the reducing terminal. Since it has strict epitope recognition specificity that it does not react if there is Glc instead of GlcNAc (FIG. 4), it is believed that very high specificity is achieved compared to an antibody of a related art.

Furthermore, according to the measurement result by ELISA of the 241-5-2 antibody in Non Patent Literature 6 (page 302), at least 50 μg of Fetuin was needed for Fetuin detection. On the other hand, the FR9 antibody of the present invention allows detection of an extremely small amount of Fetuin (about 15 ng) (FIG. 1B). Based on the result, also in terms of the affinity for the CDw75 sugar chain antigen, it can be said that the detection sensitivity which is at least 3000 times higher than the 241-5-2 antibody of Non Patent Literature 6 is achieved by the FR9 antibody of the present invention.

INDUSTRIAL APPLICABILITY

In addition to an antibody pharmaceutical for influenza and an antibody pharmaceutical or a diagnostic agent used for B-cell lymphoma, progressive gastric cancer, or colorectal cancer, use can be made for a reagent for basic research, a system for analysis of sugar chain like sugar chain array, or a kit for pathological analysis.

| 0-1 | Form PCT/RO/134 (SAFE) | PCT-SAFE |
|---|---|---|
|  | Indications relating to deposited microorganism or other biological materials (PCT Rule | Version 3.51.060.236a MT/FOP 20131001/0.20.5.21 |
| 0-1-1 | 13.2) were made as described in the right column. |  |
| 0-2 | International application No. |  |
| 0-3 | Document Code of Applicant or Agent | SJU5165240WO |
| 1 | The following descriptions are related to the microorganism or biological materials that are referred to in the detailed description of the invention. |  |

-continued

| | | |
|---|---|---|
| 1-1 | Paragraph No. | 0010, 0023, 0043 |
| 1-3 | Description of Deposit | NPMD Patent Microorganisms Depositoary (NPMD), |
| 1-3-1 | Name of Person in Depository Organization | National Institute of Technolory and Evaluation (NITE) |
| 1-3-2 | Address of Depository Organization | #122, 2-5-8 Kazusakamatari, Kisarazu-shi, Chiba 292-0818, Japan |
| 1-3-3 | Deposit date | Jan. 21, 2013 |
| 1-3-4 | Accession number | NPMD NITE BP-01516 |
| 1-5 | Designated stated for which indications are made | All designated states |

For Receiving Office use only

| | | |
|---|---|---|
| 0-4 | This sheet was received together with the international application (yes/no) | ✓ |
| 0-4-1 | Authorized officer | Tomio SEKIGUCHI |

-continued

For International Bureau use only

| | | |
|---|---|---|
| 0-5 | This sheet was received by the International Bureau on | |
| 0-5-1 | Authorized officer | |

The invention claimed is:

1. An anti-CDw75 monoclonal antibody produced by hybridoma FR9 deposited under Accession No. NITE BP-01516, or a fragment thereof.

2. A composition comprising the anti-CDw75 monoclonal antibody or a fragment thereof according to claim 1, and a pharmaceutically acceptable carrier.

3. A kit for determining morbidity and/or tumor malignancy of gastric cancer or colorectal cancer, the kit comprising as an effective component the anti-CDw75 monoclonal antibody or a fragment thereof according to claim 1.

4. Hybridoma FR9 deposited under Accession No. NITE BP-01516 which produces anti-CDw75 monoclonal antibody.

* * * * *